(12) United States Patent
Watson et al.

(10) Patent No.: US 11,965,893 B2
(45) Date of Patent: Apr. 23, 2024

(54) BIOMARKER FOR PREECLAMPSIA

(71) Applicant: The Queen's University of Belfast, Belfast (GB)

(72) Inventors: Chris Watson, Belfast (GB); Timothy Lyons, Belfast (GB); Alice Cheung, Belfast (GB); Clare Kelly, Belfast (GB)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 17/811,167

(22) Filed: Jul. 7, 2022

(65) Prior Publication Data

US 2023/0133540 A1   May 4, 2023

Related U.S. Application Data

(63) Continuation of application No. 16/487,179, filed as application No. PCT/EP2018/054194 on Feb. 21, 2018, now abandoned.

(30) Foreign Application Priority Data

Feb. 21, 2017   (GB) ..................... 1702792

(51) Int. Cl.
*G01N 33/68*   (2006.01)
*C07K 16/18*   (2006.01)

(52) U.S. Cl.
CPC .......... *G01N 33/689* (2013.01); *C07K 16/18* (2013.01); *C07K 2317/34* (2013.01); *G01N 2333/471* (2013.01); *G01N 2800/368* (2013.01); *G01N 2800/50* (2013.01)

(58) Field of Classification Search
None
See application file for complete search history.

(56) References Cited

U.S. PATENT DOCUMENTS

| 7,097,983 B2 | 8/2006 | Markovsky et al. |
| 2015/0132226 A1 | 5/2015 | Greenwood et al. |
| 2017/0322228 A1 | 11/2017 | Horiuchi et al. |
| 2018/0267044 A1 | 9/2018 | Mills et al. |

FOREIGN PATENT DOCUMENTS

| WO | 2011015602 | 2/2011 |
| WO | 2013169751 | 11/2013 |

OTHER PUBLICATIONS

International Search Report and Written Opinion in corresponding PCT Application No. PCT/EP2018/054194, dated May 29, 2018.
Pergialiotis, et al., "An evaluation of calprotectin as serum marker of preeclampsia: a systematic review of observational studies", Inflamm Res., Feb. 2016, 65(2), pp. 95-102.
Anonymous, "Anti-LRG1 antibody ab63836" Sep. 13, 2002, retrieved from: https://www.abcam.com/lrg1lrg-antibody-ab63836.html.
Office Action in corresponding U.S. Appl. No. 16/487,179, dated Jan. 7, 2022.
Cheung, et al., "LRGI as a predictive marker for pre-eclampsia in women with type 1 diabetes", Diabetologia, 2017, 60, p. S428.

*Primary Examiner* — Changhwa J Cheu
(74) *Attorney, Agent, or Firm* — Hovey Williams LLP; Crissa A. Cook (57) ABSTRACT

This invention relates to the use of biomarker LRG1 as a biomarker for preeclampsia for use from the first trimester. Elevated levels of leucine-rich alpha 2 glycoprotein 1 (LRG1) can predict risk for the future development of preeclampsia or other hypertensive disorders of pregnancy. The predictive test will comprise the measurement of LRG1 protein, peptide fragment, DNA or RNA, from either blood, plasma, serum, urine, saliva or amniotic fluid. The invention provides a method and a test kit to assess the risk of pre-eclampsia in pregnant woman. The method or test can utilise antibodies to measure levels of LGR1 in a sample.

10 Claims, 7 Drawing Sheets

Specification includes a Sequence Listing.

BIOMARKER FOR PREECLAMPSIA

RELATED APPLICATIONS

This application is a continuation of U.S. Ser. No. 16/487,179, filed Aug. 20, 2019, which is the U.S. National Stage of International Patent Application No. PCT/EP2018/054194, filed Feb. 21, 2018, each of which is hereby incorporated by reference in its entirety, and which claim priority to United Kingdom Patent Application No. 1702792.1, filed Feb. 21, 2017.

SEQUENCE LISTING

The sequences listed in the accompanying Sequence Listing are presented in accordance with 37 C.F.R. 1.822. The Sequence Listing is submitted as a Standard ST.26 compliant XML, file entitled "Sequence Listing 52693," created on Jul. 7, 2022, as 3,638 bytes, which is incorporated by reference herein.

This invention relates to a biomarker for preeclampsia. More specifically the invention relates to the use of leucine-rich alpha 2 glycoprotein 1 (LRG1) as a biomarker to predict risk for the future development of preeclampsia or other hypertensive disorders of pregnancy. The predictive test will comprise the measurement of LRG1 protein, peptide fragment, DNA, or RNA, from a biological sample, for example, whole blood, plasma, serum, urine, saliva or amniotic fluid.

FIELD OF THE INVENTION

Preeclampsia (PE) is a leading complication of pregnancy, causing the death of 75,000 mothers and 500,000 babies annually worldwide. PE manifests as new-onset hypertension (>140/90 mmHg) developing after 20 weeks of gestation, classically accompanied by new-onset proteinuria (>300 mg/24 hr) (Brown et al. 2001), and/or, by more recent definition, by other manifestations of organ damage (ACOG Task Force, 2013). PE remains a major challenge: it is without a clearly understood cause or mechanism, and without effective predictive tests or therapies. Standards of care are resource-intensive, and although maternal outcomes have greatly improved in developed nations, fetal mortality remains high. Untreated, PE may lead to life-threatening seizures (eclampsia), cerebral hemorrhage, and acute renal failure. PE increases the need for neonatal intensive care. Subsequently, it is associated with cardiovascular and metabolic health problems later in life for both mother and baby. Consequently, PE is associated with enormous personal, economic, and health burdens (Hakim et al., 2013).

BACKGROUND TO THE INVENTION

The primary target disease for this technology is preeclampsia (PE). PE is one of the leading causes of maternal and neonatal morbidity and mortality worldwide, with incidence rates ranging from 2-5% of all pregnancies in the Western Europe, the United States, and Canada. In developing countries, PE is more common, and affects 4-18% of deliveries in some parts of Africa. An estimated 76,000 maternal and 500,000 infant deaths are caused by PE and other hypertensive disorders of pregnancy each year.

PE is a disease that is unique to pregnancy. It is a multisystem disorder characterised by new onset, of high blood pressure (hypertension), excessive leakage of protein in the urine (proteinuria), and/or dysfunction of other major organ systems (e.g. liver, heart) beginning after 20 weeks gestation. When early signs are neglected, it can lead to serious complications, most notably the critical life-threatening condition known as eclampsia (uncontrolled hypertension and seizures). Presently, management consists of vigilance to detect the early stages, symptomatic treatment to prolong the pregnancy, and early delivery. Indeed, 'delivery' is often termed the 'only cure for PE'—clearly an unsatisfactory situation. Our ability to predict PE is poor, and safe, effective measures for treatment or prevention are entirely lacking. The difficulty in predicting PE is inevitable, since basic disease mechanisms are poorly understood.

Currently, there are some tests available to predict PE, but these are unsatisfactory, being useful only relatively late in gestation and close to disease onset, and/or being insufficiently sensitive or specific. As the understanding of the mechanisms underlying PE improve, and as new interventions become available for assessment, it will be increasingly important to identify, early in pregnancy, those women at highest risk. We already know that PE is more common among certain categories of women, including those who have diabetes prior to conception ('pre-gestational diabetes'). Thus, an otherwise healthy woman with Type 1 diabetes has a four-fold increased risk of developing PE than her non-diabetic counterpart (~20% vs ~5%). In designing prospective studies of pregnancy, a focus on women who at high risk for PE, such as those with Type 1 diabetes, brings the efficiency of a high case yield, yet may still reveal mechanisms and biomarkers relevant to PE in general. The identification of new disease mechanisms is an urgent goal. These mechanisms will include maternal factors present early in pregnancy (and indeed before conception) and foetal/placental factors that are operative later.

Current clinical management is reliant on pragmatic assessment of known risk factors, with close monitoring of blood pressure and urinary protein. There are no interventions that can prevent PE (low dose aspirin started early in pregnancy may be partially effective, reducing incidence by an estimated, and inadequate, 17-25% (Askie et al., 2007; Duley et al., 2007; Roberge et al., 2012; Henderson et al., 2014). No specific treatments are available that target underlying disease mechanisms. Once diagnosed, typically after 30 weeks gestation, patients receive symptomatic alleviation (antihypertensives, anticonvulsants), but this is not always effective. Delivery, often premature, represents the only "cure".

Although PE becomes manifest late in pregnancy, it is thought to result from a combination of underlying maternal characteristics and, within a specific pregnancy, events occurring around the time of 'placentation' (establishment of the placenta) in the first trimester. Deficiencies in placentation may only become clinically manifest later, when fetal demands rise dramatically in the third trimester, but could be detectable much earlier if appropriate biomarkers can be defined.

There is a need for early biomarkers for PE to stratify patients for assessment of new interventions, and to guide intensity of ante-natal care. Currently, the principal candidate biochemical biomarker in early gestation is placental growth factor (PlGF), with others such as PAPP-A, PP13, and alpha-fetoprotein having lesser roles. PlGF has greatest utility when combined with mean arterial pressure, uterine Doppler studies, and maternal clinical factors. From late-second/early third trimesters, sFlt and Endoglin, in addition to PlGF are of value, but there are still many false positive results (Zeisler NEJM 2016). Better biomarkers are needed.

At present, traditional risk stratification based on patient history and clinical characteristics predicts only ~30% of PE cases (Audibert et al., 2010). With the identification of candidate plasma or serum factors that may reflect impaired trophoblast health, there has been great effort to find better ways for early prediction and/or detection. As mentioned above, some algorithms have combined several candidate biochemical markers, and/or have added clinical information (e.g. maternal mean arterial pressure, data from uterine artery Doppler studies), since no biomarker by itself is sufficiently discriminatory.

The ability to predict PE in the first trimester is theoretically possible since, as stated above, inherent maternal factors and deficiencies in placentation are thought to 'set the stage' for later overt disease. Such ability would be of immense value in planning ante-natal care, and by enabling patient stratification, in assessing the efficacy of new interventions. In this regard, with respect to biochemical markers, work to date has focused on several proteins of fetal (trophoblast) origin. The most promising of these is Placental Growth Factor (PlGF) (O'Gorman, ACOG 2016). Other candidate circulating factors, including Pregnancy-Associated Plasma Protein A (PAPP-A), and $\alpha$-fetoprotein ($\alpha$-FP) have been combined with plasma PlGF, and marketed as a predictive kit (PreeclampsiaScreen™/T1, Perkin-Elmer: http://www.ntdlabs.com/preeclampsia-providers). However, since then, evidence suggests that PAPP-A and $\alpha$-FP do not add useful predictive power (Bredaki et al., 2016; O'Gorman et al., 2016), and previously, another candidate biomarker, Placental Protein 13 (PP-13), was also shown to have inadequate predictive power (Akolekar et al., 2009). At present, therefore, the best model is derived from an algorithm in which plasma PlGF, measured at weeks gestation, is combined with maternal mean arterial pressure (MAP), uterine Doppler findings, and an extensive suite of maternal data (age, weight, height, racial origin, inter-pregnancy interval, gestational age at delivery and presence/absence of preeclampsia in previous pregnancies, method of conception, and presence/absence of chronic hypertension, diabetes mellitus, systemic lupus erythematosus, or antiphospholipid syndrome (Wright et al., 2015)) (O'Gorman et al., 2016). Using this model, the predictive power of the maternal factors alone (as defined by Wright et al., 2015) is significantly improved by addition of PlGF, MAP, and uterine Doppler data; likewise, that of PlGF alone is improved by the other parameters (O'Gorman et al. 2016). In summary, although some first trimester predictive algorithms exist, they are imperfect and complex. Better and more convenient means for the early prediction of PE are needed.

The roles of circulating anti-antiangiogenic factors, specifically sFlt1 (which binds and thus inhibits pro-angiogenic VEGF) must also be mentioned. These are best-established circulating factors for the prediction of PE, but only become useful a short time before PE develops. Thus, after ~20 weeks gestation, the sFlt1/PlGF ratio (www.cobas.com, Roche, Switzerland) can predict PE with a sensitivity of 82% and specificity of 95% (Verlohren et al. 2014), but is of almost no value in the first trimester and limited value until later in the second trimester. Emphasizing this limitation, Zeisler et al. (NEJM 2016) confirmed the utility of sFlt1/PlGF ratio, but only in the context of women at 24-36 wks gestation who were already suspected of having early clinical PE, with actual PE onset only one week later. Thus, sFlt-1 and related measures are useful later in pregnancy, but early predictors are needed.

SUMMARY OF THE INVENTION

The invention relates to the use of leucine-rich alpha 2 glycoprotein 1 (LRG1) as a biomarker to predict risk for the future development of preeclampsia or other hypertensive disorders of pregnancy.

The predictive test will comprise the measurement of LRG1 protein, peptide fragment, DNA or RNA, from blood, plasma, serum, urine, saliva or amniotic fluid.

According to the present invention there is provided a marker for Pre-Eclampsia (PE) comprising Leucine-rich alpha 2 glycoprotein 1 (LRG1).

The invention also provides the use of LRG1 in an in vitro method for prediction of PE. The method can be used to determine if a pregnant woman is at increased risk of developing PE. The method can also be used to determine risk pre-pregnancy, prior to conception.

The invention can also be used to monitor response to treatment for PE.

The invention provides the use of LRG1 as a diagnostic biomarker for PE.

The inventors surprisingly recognised that LRG1 can be used as a biomarker for PE from as early as the first trimester of pregnancy and can be used in the second and third trimesters also.

The invention also provides a method for predicting whether a pregnant woman is susceptible to PE, the method including the step of testing a biological sample from the woman for elevated levels of LRG1.

Preferably the sample is plasma or serum.

Elevated levels of LRG1 are typically at least 30 mcg/ml LRG1 in plasma and serum.

More preferably the elevated levels are typically greater or equal to 35 mcg/ml LRG1 in plasma and serum.

More preferably the elevated levels are greater or equal to 40 mcg/ml LRG1 in plasma and serum.

More preferably the elevated levels are greater or equal to 45 mcg/ml LRG1 in plasma and serum.

More preferably the elevated levels are greater or equal to 50 mcg/ml LRG1 in plasma and serum.

More preferably the elevated levels are greater or equal to 55 mcg/ml LRG1 in plasma and serum.

More preferably the elevated levels are greater or equal to 60 mcg/ml LRG1 in plasma and serum.

An elevated level of LRG1 during pregnancy for any one individual can be considered to be a level that is greater than or equal to an increase of greater or equal to 15% over normal pre-pregnancy level for that individual.

Statistical methods for determining if the abundance of a protein of interest is increased or decreased relative to a reference sample are well known in the art.

In various embodiments, determination of the level of LRG1 in a biological fluid, such as whole blood, plasma, serum, saliva, urine or amniotic fluid, may be performed using a variety of methods known to those of skill in the art.

In various embodiments, in a direct comparative analysis, the reference sample and test sample may be treated exactly the same way, in order to correctly represent the relative abundance of LRG1 and obtain accurate results.

For example, in various embodiments, the proteins present in the biological samples may be separated by 2D-gel electrophoresis according to their charge and molecular weight. For instance, the proteins may first be separated by their charge using isoelectric focusing (one-dimensional gel electrophoresis), for example using immobilized pH-gradient (IPG) strips, which are commercially available.

In various embodiments, the second dimension may be an SDS-PAGE analysis, where the focused IPG strip may be used as the sample. After two-dimensional gel electrophoresis separation, proteins may then be visualized with conventional dyes, such as Coomassie Blue or silver staining, and imaged using known techniques and equipment, such as, for example Bio-Rad GS800 densitometer and PDQUEST™ software.

In some embodiments, individual spots may then be cut from the gel, de-stained, and subjected to tryptic digestion, allowing the peptide mixtures to be analyzed by mass spectrometry (MS). Alternatively, in some embodiments, the peptides may be separated, for example by capillary high pressure liquid chromatography (HPLC) and may be analyzed by MS either individually, or in pools. If desired, in some embodiments, the amino acid sequences of the peptide fragments and the proteins from which they derived may be determined. Although it is possible to identify and sequence all or some of the proteins present in a proteomic profile, this typically is not necessary for the diagnostic use of the methods disclosed herein.

As discussed above, in various embodiments, a diagnosis of or risk of preeclampsia may be based on characteristic similarities or differences between a reference sample and a test sample. For example, in various embodiments, if the proteomic profile is presented in the form of a mass spectrum, the expression signature may be a peak representing LRG1 that differs, qualitatively or quantitatively, from the mass spectrum of a corresponding normal sample. Thus, any statistically significant change in the amplitude or shape of an existing peak may reflect a change in a level of LRG1 relative to a control.

Other embodiments may utilize protein arrays to monitor LRG1 levels, enabling high-throughput analysis. Protein arrays are known to those of skill in the art, and generally are formed by immobilizing proteins, such as antibodies specific for proteins of interest, like LRG1, on a solid surface, such as glass, silicon, nitrocellulose, or PVDF using any of a variety of covalent and non-covalent attachment chemistries well known in the art. The arrays may be probed with fluorescently labeled proteins from two different sources, such as normal and test samples, and fluorescence intensity may reflect the expression level of a target protein, such as LRG1.

Various embodiments also may use any of various immunoassay formats for quantification of protein expression levels. In general, immunoassays may be homogeneous or heterogeneous. For instance, in various embodiments, an enzyme-linked immunosorbent assay (ELISA) may be used to quantify protein expression. In one example, in a "sandwich" assay, a solid surface may be coated with a solid phase antibody, and the test sample may be allowed to react with the bound antibody. Any unbound antigen may then be washed away, and a known amount of enzyme-labeled antibody may then be reacted. The label may then be quantified as a direct measurement of the amount of protein of interest present in the sample.

In some embodiments, ELISA may also be used as a competitive assay. For example, in a competitive assay, the test sample containing the protein of interest may be mixed with a precise amount of enzyme-labeled protein of interest, and both may compete for binding to an antibody attached to a solid surface. In various embodiments, excess free enzyme-labeled protein may be washed off before the substrate for the enzyme is added, and the color intensity resulting from the enzyme-substrate interaction may be used as a measure of the amount of protein of interest in the test sample.

Various other embodiments may quantify the proteins of interest using an Enzyme Multiplied Immunoassay Technique (EMIT), which may include a test sample, enzyme-labeled molecules of the proteins of interest, antibodies specific to the proteins of interest, and a specific enzyme chromogenic substrate. In various embodiments, an excess of the specific antibodies may be added to the test sample, and the proteins of interest may then bind to the antibodies. In various embodiments, a measured amount of the corresponding enzyme-labeled proteins may then be added to the mixture, and antibody binding sites not occupied by proteins of interest from the test sample may be occupied with molecules of the enzyme-labeled protein. As a result, in various embodiments, enzyme activity may be reduced because only free enzyme-labeled protein can act on the substrate, and the amount of converted substrate may reflect the amount of free enzyme left in the mixture. In various embodiments, a high concentration of the protein of interest in the sample may result in higher absorbance readings.

The LRG1 detection assay may include, but not restricted to, antibodies that specifically bind to the following epitope regions of LRG1 protein: GLKALGHLSGNRLRKL; AGPEAVKGQTLLAVAKSQ.

Various other embodiments include immunoassay kits for the quantification of the proteins of interest in a test sample. In various embodiments, these kits may include, in separate containers, one or more monoclonal or polyclonal antibodies having binding specificity for LRG1, and, optionally, anti-antibody immunoglobulins, particularly labeled anti-antibody immunoglobulins.

Also disclosed herein are capture devices and sample collection kits for use in the disclosed methods.

In some embodiments, the disclosed methods may be carried out using a sample capture device, such as a lateral flow device (for example a lateral flow test strip) that may allow quantification of LRG1. Lateral flow devices are available in numerous different configurations, but in one example, a test strip may include a flow path from an upstream sample application area to a test site, such as from a sample application area through a mobilization zone to a capture zone. In various embodiments, the mobilization zone may contain a mobilizable marker that may interact with the protein of interest, and the capture zone may contain a reagent that binds the protein of interest for detection and/or quantification. In other embodiments, exemplary sample collection kits may include an absorbent medium, such as filter paper, that may include indicia for the placement of the test sample on the medium. Such kits also may include a lancing device for obtaining a blood sample from a subject, and optionally, a mailer for sending the test sample to a physician or laboratory for analysis. Such sample collection kits may be used, for example, during standard prenatal exams, such as the eight week, twelve week, sixteen week, twenty week, twenty-four week, twenty-eight week, thirty week, or subsequent-week visit, and/or sample collection may be performed when blood is obtained for other standard prenatal tests.

LRG1 testing can be combined with other tests which have been found to some extent predictive of PE either early or late in gestation. These other tests can be chosen from sFlt-1, Endoglin, PlGF, PAPP, PP13, α-FP, sRAGE (Receptor for Advanced Glycation End-products). Also lipoprotein characteristics as follows: low density lipoprotein (LDL)-cholesterol, particle concentrations of total LDL and large (but not small) LDL, serum ApoB, ApoB:ApoAI ratio, ApoCIII ratio. Also, urinary NGAL:creatinine ratio, eGFR, FABP4, leptin, adiponectin, uterine artery Doppler studies and mean maternal arterial pressure.

Preferred markers of interest are leptin, adiponectin (total and high molecular weight), FABP4, Zonulin, BNP and Troponin.

As this technology is developed for the market it is possible that the calibration range can change between the discovery stage which uses commercially available Research Only Use, and a CE-marked diagnostic product where the calibration for kits sold will be assigned via a reference material. Also proprietary antibodies may be used and the kits adapted accordingly.

DETAILED DESCRIPTION OF THE INVENTION

The invention is exemplified in the following non limiting studies and figures.

BACKGROUND STUDIES

The present inventors conducted a prospective study, choosing to study women with and without Type 1 diabetes ('Markers and Mechanisms for Pre-Eclampsia in Diabetes' or MAMPED; PI: Lyons). Diabetic women are of interest because of their high PE case yield: a major advantage in a prospective study Women were studied at 12, 22, and 32 weeks' gestation. Clinical as well as biochemical data were collected. We assessed some known candidate risk factors. As expected from prior studies of non-diabetic women, anti-angiogenic factors including sFlt and Endoglin, and angiogenic PlGF were predictive of PE, but only after 28 weeks gestation, i.e. soon before clinical onset of PE. For the reasons outlined above, we were particularly interested to identify first- or second-trimester characteristics associated with the later onset of PE. Several factors have emerged that are related to maternal dyslipidaemia and insulin resistance. We assessed markers of heart failure/cardiac dysfunction (BNP and Troponin) but found these to be unrelated to subsequent PE.

The prevalence of PE is increased 3- to 6-fold by maternal Type 1 diabetes mellitus (T1 DM), even in women with no pre-gestational microalbuminuria or hypertension (Yu et al., 2009; Powers et al., PLoS One, 2010; Holmes et al., 2013). This high prevalence of PE in T1 DM women brings an opportunity in that it facilitates human prospective studies with a high case-yield, and thus a manageable time-frame. We designed and conducted such a study (Markers and Mechanisms for Pre-Eclampsia in Diabetes' or MAMPED; PI: Lyons) to seek new knowledge of biomarkers and mechanisms for PE in general, by capitalizing on the high case yield from women with diabetes. This rationale is supported by the congruence of findings between diabetic and non-diabetic women for antiangiogenic predictive factors, as described above. For reference values, MAMPED included a group of healthy, non-diabetic women who had normal, uncomplicated pregnancies.

Markers and Mechanisms of Pre-Eclampsia in T1DM (MAMPED; PI Lyons).

MAMPED enrolled 151 pregnant women with documented uncomplicated pre-gestational T1DM (free of hypertension or microalbuminuria) and 24 non-diabetic pregnant women, recruited from six medical centers in three countries (Norway, Australia, USA). Of the T1DM subjects, 20% developed PE, vs ~4% (i.e. one) of the non-diabetic subjects, consistent with the high risk conferred by diabetes. Complete clinical data and specimens (plasma, serum and urine) were collected at three study visits (~11-13, 20-22, and 30-32 wks of gestation) and at term (~38 wks). The non-diabetic control group was included to provide reference values, enabling comparisons of data between T1DM patients and the low-risk non-diabetic group. MAMPED has resulted in many high-impact publications (Yu et al., 2009; Azar et al., 2011; Basu et al., 2012; Yu et al., 2012; Du et al. 2013), including the first to define predictive roles of angiogenic/anti-angiogenic factors in early third-trimester diabetic pregnancy (Yu et al., 2009). The present inventors also found some first and second trimester parameters that were significantly associated with subsequent PE, but not to an extent that would be useful clinically. For example, we observed lower plasma levels of soluble receptor for advanced glycation end-products (sRAGE), and its ratio to advanced glycation endproducts (AGEs) at 12 wks in T1DM women who subsequently developed PE, possibly reflecting a higher burden of AGEs in diabetes and resultant compromise of scavenger capacity (Yu et al., 2012). In a detailed analysis of plasma lipoproteins, measuring conventional lipids, apolipoproteins, and subclasses defined by size (NMR) and apolipoprotein content (Basu et al. 2012), we found that in women with vs. without subsequent PE, low-density lipoprotein (LDL-C), particle concentrations of total LDL and large LDL, Apolipoprotein B (ApoB), and ApoB:Apolipoprotein AI (ApoAI) ratio were all increased in the $1^{st}$ and $2^{nd}$ trimesters, while peripheral lipoprotein lipolysis was decreased. This suggested that increased levels of certain cholesterol-rich particles and impaired peripheral lipolysis early in pregnancy are associated with subsequent PE. MAMPED samples were similarly used to test the utility of a novel protein, leucine-rich alpha 2 glycoprotein 1 (LRG1). This protein has never been studied during pregnancy as a predictor of PE.

Leucine-Rich Alpha 2 Glycoprotein 1 (LRG1)

Background

Leucine-rich alpha 2 glycoprotein 1 (LRG1) was identified in 1977 as a trace component of human serum, and resolution of the primary structure in 1985 indicated that it exists as a single polypeptide chain of MW approximately 45 kDa (Takahashi et al., 1985, Haupt and Baudner, 1977). The presence of a leucine at every seventh position in segments of this protein suggests the possibility of forming a leucine-zipper structure, which has been implicated in protein-DNA and protein-protein interactions (Takahashi et al., 1985). Although the precise function of LRG1 has yet to be fully elucidated, evidence to date suggests that it is associated with inflammatory responses and neutrophilic differentiation, implicated in cell migration, and linked to cellular responses to the pro-fibrotic cytokine transforming growth factor beta (TGFβ) (Zhong et al., 2015, Takemoto et al., 2015, Ha et al., 2014, Lynch et al., 2013, Serada et al., 2012, O'Donnell et al., 2002, Codina et al., 2010). In studies examining LRG1 in the context of established disease, the directional change of LRG1 levels varies in comparison to associated experimental controls. For example, it has been shown that in patients with hepatitis C, LRG1 expression in patients decrease with increasing severity of fibrotic change in diseased livers, and in a separate study involving patients with allergic airway disease, circulating LRG1 levels and TGFβR2 decrease compared to controls (Hao et al., 2016, Zhang et al., 2015b). However, in other pathological settings, circulating levels increase, including in sepsis, neurodegenerative disease, heart failure, and cancer (Hashida et al., 2016, Cavalcante Mde et al., 2016, Zhang et al., 2015a, Furukawa et al., 2015, Miyajima et al., 2013, Watson et al., 2011). Thus it is difficult to predict how expression levels of LRG1 protein might change in particular disease states, and whether or not it plays a causal role in various disease settings. In addition, all published studies have investigated LRG1 in established disease, and thus little is known about the predictive power of LRG1 as a biomarker for future disease in otherwise disease-free patients.

Figure 1:
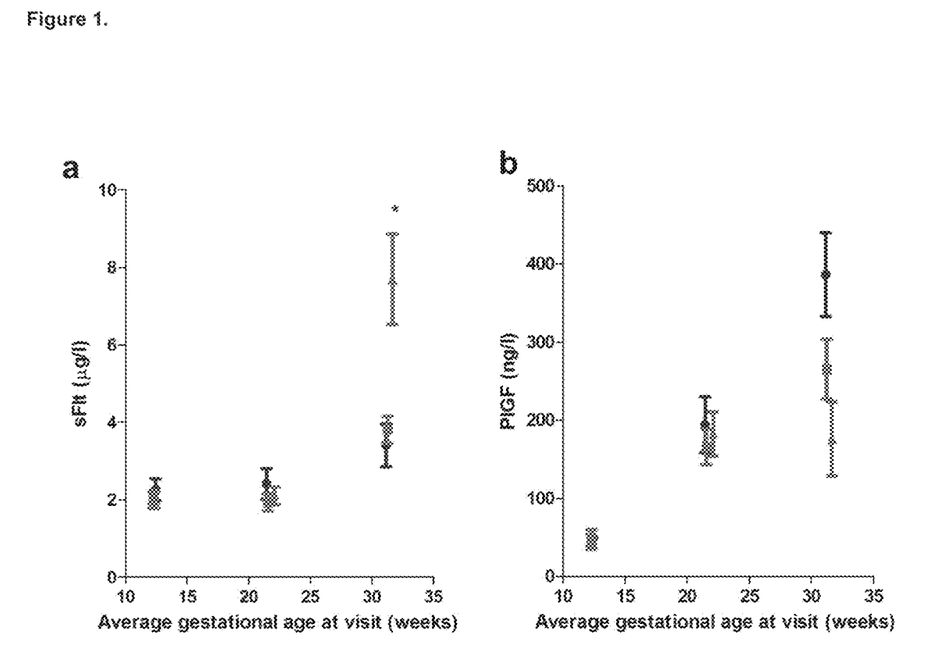
FIG. 1 shows levels of anti-angiogenic (sFlt1) and angiogenic (PlGF) markers prior to preeclampsia diagnosis. These biomarkers and their ratio are effective in predicting preeclampsia late in pregnancy
Figure 2:
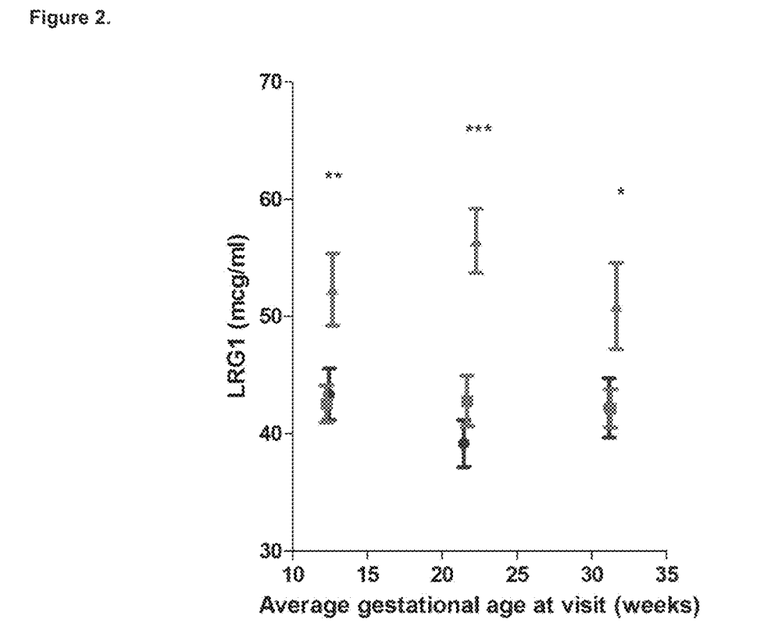
FIG. 2 shows levels of LRG1 prior to preeclampsia diagnosis

The present inventors originally set out to study LRG1 in the context of diabetes and its complications. As part of this, we explored LRG1 levels in the MAMPED pregnancy cohort of type 1 diabetic women: these women had no evidence of prior renal or hypertensive problems, as described above. This was the first-ever study to investigate LRG1 during pregnancy. Within this well-characterised cohort of pregnant women, we found little change in LRG1 level as pregnancy progressed, and we found no association of LRG1 with diabetes per se. However to our surprise, from the earliest time point (12 weeks' gestation), LRG1 levels were associated with future hypertensive complications of pregnancy. Thus, LRG1 predicted the (much) later development of preeclampsia, well before the onset of high blood pressure and clinical disease, and over a time-frame distinctly different from established angiogenic biomarkers. In women with apparently normal pregnancies who developed preeclampsia with onset after 33 weeks gestation, LRG1 levels were significantly elevated as early as 12 weeks gestation, and remained elevated at 22 and 32 weeks (FIG. 2). LRG1 thus acts as a biomarker for the future development of PE much earlier than the gold-standard PE diagnostic biomarkers, sFlt-1 and PlGF (FIG. 1). The discovery of LRG1 as an early biomarker for the future development of PE was only possible because of the longitudinal nature of the MAMPED cohort, facilitating analyses throughout the duration of pregnancy.

Figure 3:
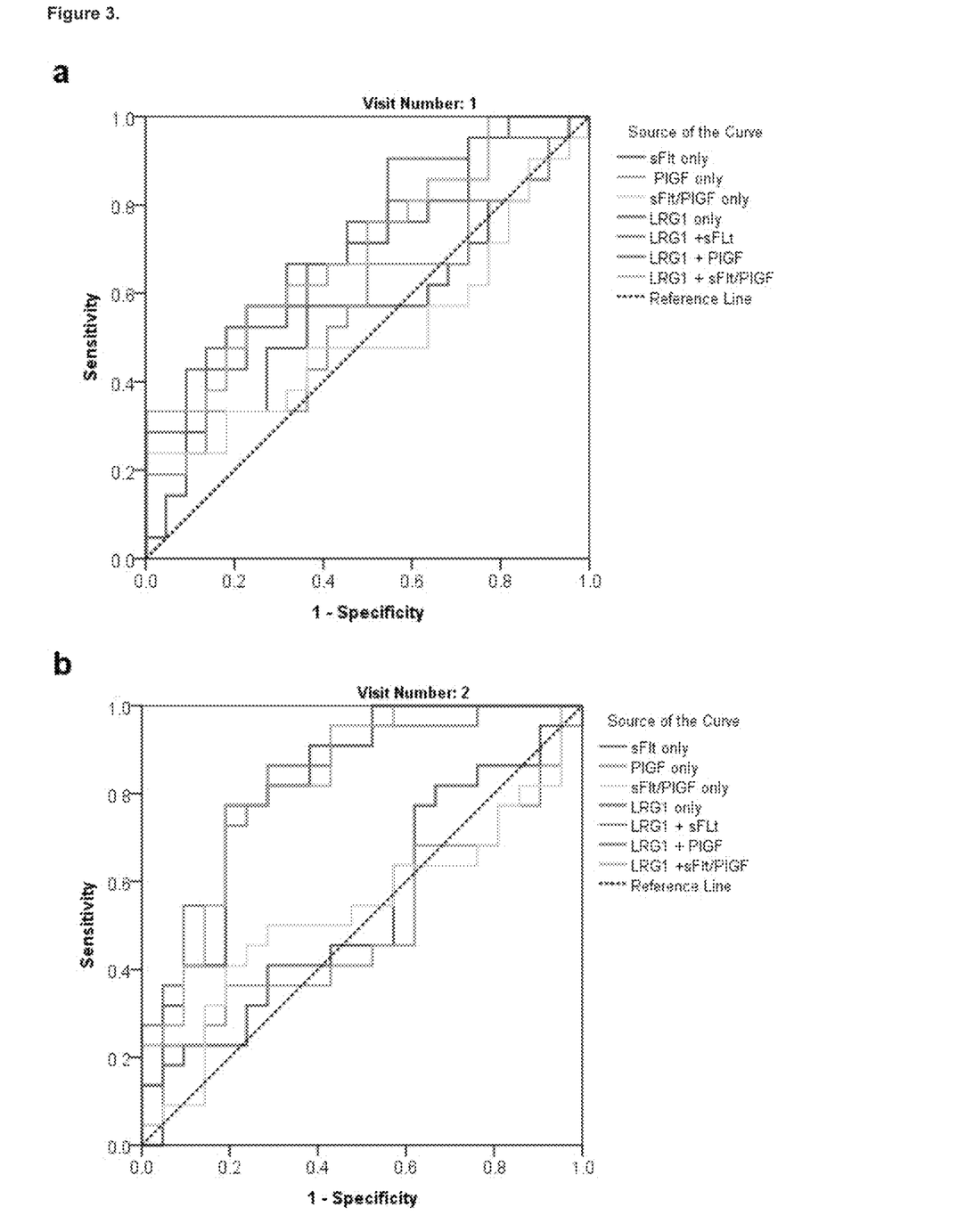
FIG. 3 illustrates ROC curves for predictive models of Preeclampsia at each study visit
Figure 4:
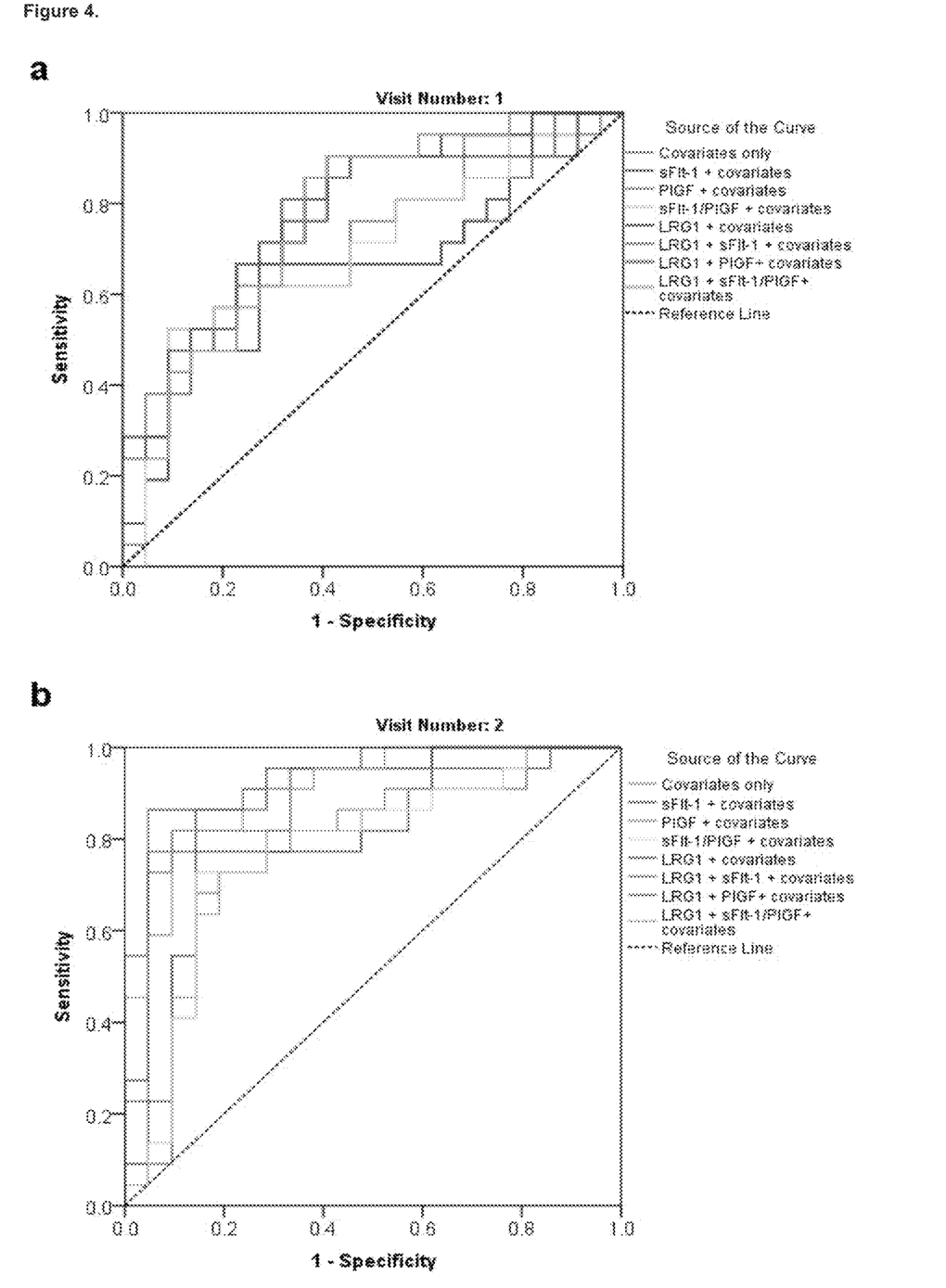
FIG. 4 illustrates ROC curves for predictive models of Preeclampsia, after adjustment of covariates, at each study visit

Various statistical models highlighting the prognostic strengths of LRG1 and how it out performs the gold standard PE biomarkers sFlt-1 and PlGF are shown in FIGS. 3 & 4 and in Tables 1~4 below. Collectively, these unique findings provide strong evidence that LRG1 could have clinical utility in the prediction, detection, and monitoring of hypertensive complications of pregnancy. It would also have a novel application in longitudinal screening in disease-free pregnant individuals as a risk predictor for preeclampsia and other hypertensive complications of pregnancy.

LRG1 as a Biomarker for PE.

The following results from the MAMPED study show that LRG1 has the capacity to serve as a useful biomarker for preeclampsia from as early as 12 weeks gestation.

FIG. 1 shows levels of anti-angiogenic (sFlt1) and angiogenic (PlGF) markers prior to preeclampsia diagnosis. These biomarkers and their ratio are effective in predicting preeclampsia late in pregnancy (MAMPED study, Yu et al. 2009)

More specifically FIG. 1 shows longitudinal changes of a sFlt, and b PlGF during gestation. Values (means±SEM) were plotted against the average gestational age at each visit. All data are prior to the onset of PE. For illustrative purposes, three groups of participants are shown. Blue symbols, non-diabetic normotensive healthy controls; green symbols, Type 1 diabetic who remained normotensive; red symbols, Type 1 diabetic who subsequently developed preeclampsia. The primary analysis compared diabetic preeclampsia and diabetic normotensive groups (*p<0.05). Secondary analyses compared diabetic normotensive vs non-diabetic normotensive groups (ns).

For sFlt1, in non-diabetic women, serum sFlt1 (FIG. 1a) was stable from visit 1 to visit 3. Among type 1 diabetic women, there was a pronounced increase (doubling) in sFlt1 between the second and third study visits in those who later developed preeclampsia, whereas in those remained normotensive throughout pregnancy, there was little change.

For PlGF, serum PlGF (FIG. 1b) increased progressively in non-diabetic normotensive women from visit 1 to visit 3. In type 1 diabetic women the increase between the second and third study visits was blunted, most markedly in women who subsequently developed pre-eclampsia.

FIG. 2 shows unpublished levels of LRG1 prior to preeclampsia diagnosis (MAMPED study, unpublished).

Longitudinal changes of LRG1 during gestation are plotted. Values (means±SEM) were plotted against the average gestational age. All study visits took place prior to the onset of PE. Values significantly different between participant groups (p<0.05) are indicated: the primary analysis compared diabetic pre-eclampsia and diabetic normotensive groups (*p<0.05, p<0.01, *p<0.001). There were no significant differences in secondary analyses comparing between diabetic normotensive vs non-diabetic normotensive groups at any study visit.

Women with type 1 diabetes who later developed preeclampsia had significantly higher LRG1 than diabetic normotensive women from the first study visit, and this persisted at the second and third study visits. No significant difference was noted between the diabetic women who remained normotensive and the non-diabetic controls at any study visit during pregnancy. Longitudinal analyses revealed significant increase in LRG1 between visit 1 and visit 2 (p<0.05), and a significant decrease between visit 2 and visit 3 (<0.05) for the diabetic women with preeclampsia. There were no longitudinal changes for the women with diabetes who remained normotensive. LRG1 significantly decreased between the first and second study visits in non-diabetic women (<0.05), but levels remained similar between the second and third visits.

FIG. 3 shows ROC curves for predictive models of preeclampsia at each study visit. The dash line: reference line indicating AUC=0.5. PlGF and sFlt-1/PlGF are logarithmically transformed to the base 10

FIG. 4 shows ROC curves for predictive models of preeclampsia, after adjustment of covariates, at each study visit. The dash line: reference line indicating AUC=0.5. PlGF and sFlt-1/PlGF are logarithmically transformed to the base 10. Adjusted for established risk factors (clinical covariates) BMI and Mean arterial pressure (MAP)

Figure 5:
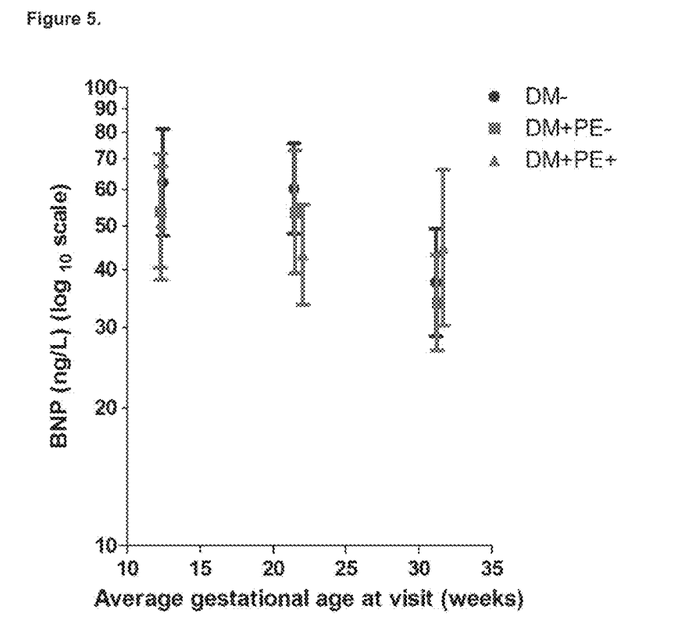
FIG. 5 shows levels of BNP, a cardiac biomarker, prior to preeclampsia diagnosis

FIG. 5 shows levels of BNP, a cardiac biomarker, prior to preeclampsia diagnosis.

FIG. 5 plots longitudinal changes of BNP over time. Values (geometric mean±95% CI of geometric mean) were plotted against the average gestational age at each visit prior to the onset of PE. See FIG. 1 for keys for both primary and secondary analyses BNP was not normally distributed. For analysis, data was logarithmically transformed. There were no significant differences in BNP levels between any of the groups at any time point, and therefore no predictive effect.

Figure 6:
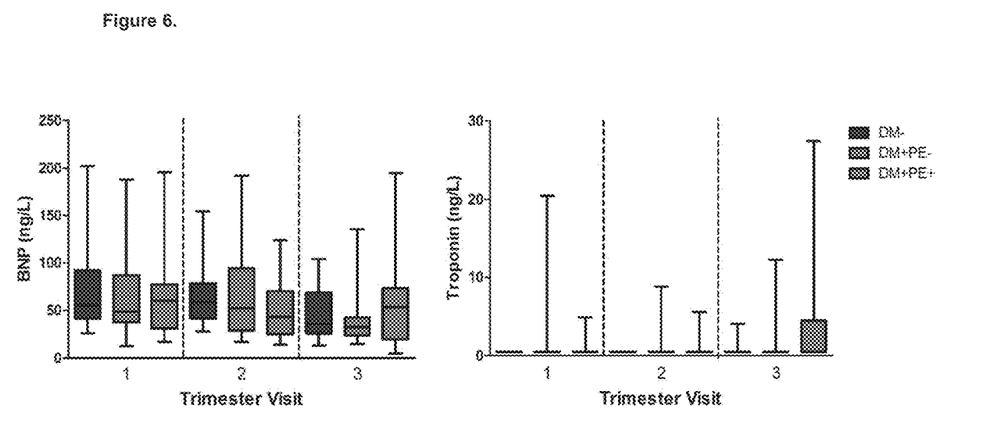
FIG. 6 shows box plots of the levels of cardiac biomarkers BNP and troponin per study visit, prior to preeclampsia diagnosis

FIG. 6 shows box plots of the levels of cardiac biomarkers BNP and troponin per study visit, prior to preeclampsia diagnosis. The lower limit of detection of Troponin is 3 ng/L. Any sample not detected was denoted as 0.5 ng/L for observational purposes. There were no significant differences in BNP or troponin levels between any of the groups at any time point

TABLE 1

| LRG1 (mcg/ml) | Unadjusted odds ratio (95% CI) | Adjusted odds ratio (95% CI)* | Area under the ROC curve without covariates [AUC (†p value)] | Area under the ROC curve with covariates* [AUC (p‡)] | IDI (¶) | NRI (§) |
|---|---|---|---|---|---|---|
| ~12 weeks gestation | 1.08 (1.01-1.16) | 1.08 (1.00-1.16) | 0.707 (0.019) | 0.769 (0.201) | 0.097 (0.035) | 0.455 (0.118) |
| ~22 weeks gestation | 1.13 (1.04-1.23) | 1.20 (1.05-1.38) | 0.824 (<0.001) | 0.919 (0.08) | 0.0252 (<0.001) | 1.01 (<0.001) |
| ~32 weeks gestation | 1.06 (1.00-1.13) | 1.10 (1.01-1.20) | 0.638 (0.108) | 0.900 (0.180) | 0.122 (0.014) | 0.848 (0.001) |

ROC: receiver operating characteristic; IDI: integrated discrimination improvement; NRI: net reclassification improvement.
*Adjusted for established risk factors ('covariates'): Body Mass Index (BMI) and Mean arterial pressure (MAP).
†Relative to AUC of 0.5, for a logistic model containing only LRG1 at current visit.
‡Relative to AUC of 0.676, 0.781, and 0.843 for a logistic model containing covariates only per visit
¶Addition of LRG1 resulted in statistically significant improvement in predicted risk of preeclampsia at all three study visits.
§Addition of LRG1 resulted in statistically significant improvement in the reclassification of preeclampsia risk at the second and third study visits.

ROC: receiver operating characteristic; 101: integrated discrimination improvement; NRI: net reclassification improvement.
*Adjusted for established risk factors ('covariates): Body Mass Index (BMI) and Mean arterial pressure (MAP).
† Relative to AUC of 0.5, for a logistic model containing only LRG1 at current visit.
‡ Relative to AUC of 0.676, 0.781, and 0.843 for a logistic model containing covariates only per visit
¶ Addition of LRG1 resulted in statistically significant improvement in predicted risk of preeclampsia at all three study visits.
§ Addition of LRG1 resulted in statistically significant improvement in the reclassification of preeclampsia risk at the second and third study visits.

The unadjusted odds ratios (i.e. assessing LRG1 by itself) showed that for every unit increase in LRG1, the risk of developing PE increased by 8%, 13%, and 6% at study visits 1, 2, and 3 respectively. In order to derive the best model, the LRG1 data were corrected for two simple maternal factors, BMI and MAP. The adjusted odds ratios indicate that, keeping all other covariates equal, for every unit increase in LRG1, the risk of developing PE increased by 8%, 20%, and 10% at study visits 1, 2, and 3 respectively. LRG1 remains significantly associated with preeclampsia after controlling for established risk factors. The addition of LRG1 to a model of clinical maternal risk factors improved the predictive value at all three study visits. The IDI and NRI statistic show that the

| | Visit 1 | | Visit 2 | | Visit 3 | |
|---|---|---|---|---|---|---|
| Variable(s) in model | Area under the ROC curve | p value* | Area under the ROC curve | p value* | Area under the ROC curve | p value* |
| sFlt only | .556 | .528 | .541 | .644 | .702 | .020 |
| PlGF only | .561 | .496 | .496 | .961 | .692 | .027 |
| sFlt/PlGF only | .511 | .903 | .530 | .734 | .728 | .009 |
| LRG1 only | .703 | .022 | .820 | <0.001 | .629 | .139 |
| LRG1 + sFLt | .703 | .022 | .827 | <0.001 | .821 | <0.001 |
| LRG1 + PlGF | .721 | .013 | .818 | <0.001 | .734 | .007 |
| LRG1 + sFlt/PlGF | .703 | .022 | .825 | <0.001 | .784 | .001 | addition of LRG1 significantly improved the discrimination between women who developed PE and those who remained normotensive (at all three visits), and the correct reclassification of women who developed PE and those who remained normotensive.

Table 2 (see also FIG. 3)—shows the areas under the ROC curve models including angiogenic/anti-angiogenic factors and/or LRG1 (MAMPED study, unpublished)

*p value relative to area under the ROC curve of 0.5

PlGF and sFlt-1/PlGF are logarithmically transformed to the base 10

In general, the ROC curves show that LRG1 alone is a better predictor of PE than the angiogenic/anti-angiogenic factors, or their ratio, at the first two study visits. The area under the ROC curve of a model including the angiogenic/anti-angiogenic factors improves after the addition of LRG1 at all study visits.

Table 3 (see also FIG. 4)—Areas under the ROC curve models including angiogenic/anti-angiogenic factors and/or LRG1 after adjustment of covariates (MAMPED study, unpublished).

A) Comparing to a model of covariates (BMI, mean arterial pressure) only, per visit

| Variables in model | Visit 1 | | Visit 2 | | Visit 3 | |
|---|---|---|---|---|---|---|
| | Area under the ROC curve | p value | Area under the ROC curve | p value | Area under the ROC curve | p value |
| Covariates only | .680 | | .773 | | .873 | |
| sFlt-1 + covariates | .682 | .777 | .790 | .472 | .899 | .361 |
| PlGF + covariates | .714 | .345 | .777 | .480 | .877 | .853 |
| sFlt-1/PlGF + covariates | .699 | .524 | .777 | .762 | .877 | .879 |
| LRG1 + covariates | .768 | .201 | .916 | .078 | .905 | .429 |
| LRG1 + sFlt-1 + covariates | .771 | .218 | .916 | .046 | .946 | .105 |
| LRG1 + PlGF + covariates | .768 | .224 | .909 | .082 | .905 | .411 |
| LRG1 + sFlt-1/PlGF + covariates | .775 | .202 | .907 | .070 | .911 | .371 |

*p value relative to area under the ROC curve of model of covariates (BMI and MAP) only, per visit
PlGF and sFlt-1/PlGF are logarithmically transformed to the base 10

B) Comparing to a model of equal chance (i.e. area under ROC curve=0.5)

| Variables in model | Visit 1 | | Visit 2 | | Visit 3 | |
|---|---|---|---|---|---|---|
| | Area under the ROC curve | p value | Area under the ROC curve | p value | Area under the ROC curve | p value |
| Covariates only | .680 | .044 | .773 | .002 | .873 | <0.001 |
| sFlt-1 + covariates | .682 | .041 | .790 | .001 | .899 | <0.001 |
| PlGF + covariates | .714 | .016 | .777 | .002 | .877 | <0.001 |
| sFlt-1/PlGF + covariates | .699 | .025 | .777 | .002 | .877 | <0.001 |
| LRG1 + covariates | .768 | .003 | .916 | <0.001 | .905 | <0.001 |
| LRG1 + sFlt-1 + covariates | .771 | .002 | .916 | <0.001 | .946 | <0.001 |
| LRG1 + PlGF + covariates | .768 | .003 | .909 | <0.001 | .905 | <0.001 |
| LRG1 + sFlt-1/PlGF + covariates | .775 | .002 | .907 | <0.001 | .911 | <0.001 |

In general, the ROC curves show that addition of LRG1 to a model containing established risk factors, is better at predicting PE than the addition of the angiogenic/anti-angiogenic factors, or the ratio, at all study visits. After the adjustment of covariates, the area under the ROC curves of models including the angiogenic/anti-angiogenic factors improve after the addition of LRG1, at all study visits. All models are better than a model of equal chance.

| Variable in model | Area under the ROC curve | Equal chance (classification cutoff 0.5) | | Setting specificity-90% | | Setting specificity-95% | |
|---|---|---|---|---|---|---|---|
| | | Sensitivity | Specificity | Sensitivity | Specificity | Sensitivity | Specificity |
| Visit 1 | | | | | | | |
| Covariates only | .680 | 63.64 | 77.27 | 50.00 | 90.91 | 18.18 | 96.45 |
| sFlt-1 + covariates | .682 | 66.67 | 77.27 | 52.38 | 90.91 | 19.05 | 96.45 |
| PlGF + covariates | .714 | 61.90 | 68.18 | 52.38 | 90.91 | 38.10 | 96.45 |
| sFlt-1/PlGF + covariates | .699 | 61.90 | 68.18 | 52.38 | 90.91 | 28.57 | 96.45 |
| LRG1 + covariates | .768 | 68.18 | 72.73 | 45.45 | 90.91 | 27.27 | 96.45 |
| LRG1 + sFlt-1 + covariates | .771 | 66.67 | 77.27 | 38.10 | 90.91 | 26.67 | 95.45 |
| LRG1 + PlGF + covariates | .768 | 66.67 | 68.18 | 42.86 | 90.91 | 26.67 | 95.45 |
| LRG1 + sFlt-1/PlGF + covariates | .775 | 61.90 | 68.18 | 42.86 | 90.91 | 23.81 | 95.45 |
| Visit 2 | | | | | | | |
| Covariates only | .773 | 73.91 | 80.95 | 43.48 | 90.48 | 13.04 | 95.24 |
| sFlt-1 + covariates | .790 | 77.27 | 66.67 | 60.00 | 90.48 | 22.73 | 95.24 |
| PlGF + covariates | .777 | 72.73 | 80.95 | 40.91 | 90.48 | 9.09 | 95.24 |
| sFlt-1/PlGF + covariates | .777 | 72.73 | 71.43 | 40.91 | 90.48 | 13.64 | 95.24 |
| LRG1 + covariates | .919 | 86.96 | 76.19 | 86.96 | 90.48 | 86.96 | 95.24 |
| LRG1 + sFlt-1 + covariates | .916 | 81.82 | 85.71 | 81.82 | 90.48 | 72.73 | 95.24 |
| LRG1 + PlGF + covariates | .909 | 86.36 | 76.19 | 77.27 | 90.48 | 77.27 | 95.24 |
| LRG1 + sFlt-1/PlGF + covariates | .907 | 77.27 | 90.48 | 77.27 | 90.48 | 69.09 | 95.24 |
| Visit 3 | | | | | | | |
| Covariates only | .873 | 71.43 | 87.50 | 42.86 | 91.67 | 33.33 | 95.83 |
| sFlt-1 + covariates | .899 | 71.43 | 91.67 | 71.43 | 91.67 | 47.62 | 96.83 |
| PlGF + rates | .877 | 71.43 | 87.50 | 67.14 | 91.67 | 33.33 | 96.83 |
| sFlt-1/PlGF + covariates | .877 | 71.43 | 87.50 | 71.43 | 91.67 | 33.33 | 96.83 |
| LRG1 + covariates | .905 | 80.95 | 87.50 | 71.43 | 91.67 | 52.38 | 96.83 |
| LRG1 + sFlt-1 + covariates | .946 | 85.71 | 91.67 | 85.71 | 91.67 | 76.19 | 96.83 |
| LRG1 + PlGF + covariates | .905 | 80.95 | 87.50 | 57.14 | 91.67 | 57.14 | 96.83 |
| LRG1 + sFlt-1/PlGF + covariates | .911 | 85.71 | 87.50 | 66.67 | 91.67 | 52.38 | 96.83 |

*covariates are BMI and MAP, per visit
PlGF and sFlt-1/PlGF are logarithmically transformed to the base 10

Table 4 shows Model fits were compared for different predictive algorithms, using the established factors for predicting PE (anti-angiogenic factors: sFlt, PlGF and sFlt/PlGF), before and after the addition of LRG1 by plotting receiver operating characteristic (ROC) diagrams and assessing the area under the curve (ROC-AUC). Initially the sensitivity and specificity of the models were calculated at a cut-off probability of 50%. Next we fixed the specificity to 90% or 95% (i.e. 1 in 10 or 1 in 20 tests is a false positive). At visit 1, although the ROC-AUC increased after the addition of LRG1 to all models, there was no significant improvement in the sensitivities and specificities. At visit 2, the model for predicting PE using LRG1 and covariates (BMI and MAP) had the highest AUC of 0.919, with a sensitivity of 82% and specificity of 86%, at a cut-off probability of 50%. When we fixed the specificity to either 90% or 95%, the specificity was 87%. This model performed better than other models using the anti-angiogenic markers with/without the addition of LRG1. At visit 3, the ROC-AUC tended to increase and the sensitivities improve, after the addition of LRG1 to any of the models using anti-angiogenic markers. Overall, LRG1 is a better predictor of PE compared to established anti-angiogenic factors at visit 2 and at visit 3, the addition of LRG1 to a model with anti-angiogenic factors, may improve the prediction of PE Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention is not limited to the embodiments described herein but can be amended or modified without departing from the scope of the present invention.

REFERENCES

Askie L M, Duley L, Henderson-Smart D J, Stewart L A: Antiplatelet agents for prevention of pre-eclampsia: a meta-analysis of individual patient data. Lancet 2007; 369:1791-1798

American College of Obstetricians & Gynecologists, Task Force on Hypertension in Preeclampsia: Hypertension in pregnancy. Report of the American College of Obstetricians and Gynecologists' Task Force on Hypertension in Pregnancy. Obstet Gynecol 2013; 122:1122-1131

Brown M A, Lindheimer M D, de Swiet M, Van Assche A, Moutquin J M: The classification and diagnosis of the hypertensive disorders of pregnancy: statement from the International Society for the Study of Hypertension in Pregnancy (ISSHP). Hypertens Pregnancy 2001; 20:IX-XIV Duley L, Henderson-Smart D J, Meher S, King J F: Antiplatelet agents for preventing pre-eclampsia and its complications. Cochrane Database Syst Rev 2007:CD004659

Hakim J, Senterman M K, Hakim A M: Preeclampsia is a biomarker for vascular disease in both mother and child: the need for a medical alert system. International J. Pediatrics 2013; 2013:953150

Henderson J T, Whitlock E P, O'Connor E, Senger C A, Thompson J H, Rowland M G: Low-dose aspirin for prevention of morbidity and mortality from preeclampsia: a systematic evidence review for the u.s. Preventive services task force. Ann Intern Med 2014; 160:695-703

Roberge S, Giguere Y, Villa P, Nicolaides K, Vainio M, Forest J C, von Dadelszen P, Vaiman D, Tapp S, Bujold E: Early administration of low-dose aspirin for the prevention of severe and mild preeclampsia: a systematic review and meta-analysis. Am J Perinatol 2012; 29:551-556

Akolekar R, Syngelaki A, Beta J, Kocylowski R, Nicolaides K. Maternal serum placental protein 13 at 11-13 weeks of gestation in preeclampsia Prenat Diagn 2009; 29: 1103-1108.

Audibert F, Boucoiran I, An N, Aleksandrov N, Delvin E, Bujold E, Rey E: Screening for preeclampsia using first-trimester serum markers and uterine artery Doppler in nulliparous women. Am J Obstet Gynecol 2010; 203:383 e381-388

Bredaki F E, Mataliotakis M, Wright A, Wright D, Nicolaides K H. Maternal serum alpha-fetoprotein at 12, 22 and 32 weeks' gestation in screening for pre-eclampsia. Ultrasound Obstet Gynecol 2016; 47: 466-471

O'Gorman N; Wright D; Syngelaki A; Akolekar R; Wright D; Poon L C; Nicolaides K H. Competing risks model in screening for preeclampsia by maternal factors and biomarkers at 11-13 weeks gestation. Am J Obstet Gynecol 2016; 214:103.e1-12.

Verlohren S, Herraiz I, Lapaire O, Schlembach D, Zeisler H, Calda P, Sabria J, Markfeld-Erol F, Galindo A, Schoofs K, Denk B, Stepan H: New gestational phase-specific cutoff values for the use of the soluble fms-like tyrosine kinase-1/placental growth factor ratio as a diagnostic test for preeclampsia. Hypertension 2014; 63:346-352

Wright D, Syngelaki A, Akolekar R, Poon L C, Nicolaides K H. Competing risks model in screening for preeclampsia by maternal characteristics and medical history. Am J Obstet Gynecol 2015; 213:62.e1-10.

Azar M, Basu A, Jenkins A J, Nankervis A J, Hanssen K F, Scholz H, Henriksen T, Garg S K, Hammad S M, Scardo J A, Aston C E, Lyons T J: Serum carotenoids and fat-soluble vitamins in women with type 1 diabetes and preeclampsia: a longitudinal study. Diabetes Care 2011; 34:1258-1264

Basu A, Alaupovic P, Wu M, Jenkins A J, Yu Y, Nankervis A J, Hanssen K F, Scholz H, Henriksen T, Lorentzen B, Clausen T, Garg S K, Menard M K, Hammad S M, Scardo J A, Stanley J R, Dashti A, Aston C E, Lyons T J: Plasma lipoproteins and preeclampsia in women with type 1 diabetes: a prospective study. J Clin Endocrinol Metab 2012; 97:1752-1762

Basu A, Yu J Y, Jenkins A J, Nankervis A J, Hanssen K F, Henriksen T, Lorentzen B, Garg S K, Menard M K, Hammad S M, Scardo J A, Aston C E, Lyons T J: Trace elements as predictors of preeclampsia in type 1 diabetic pregnancy. Nutrition Research 2015; 35:421-430

Du M, Basu A, Fu D, Wu M, Centola M, Jenkins A J, Hanssen K F, Garg S K, Hammad S M, Scardo J A, Aston C E, Lyons T J: Serum inflammatory markers and preeclampsia in type 1 diabetes: a prospective study. Diabetes Care 2013, 36:2054-2061

Holmes V A, Young I S, Patterson C C, Maresh M J, Pearson D W, Walker J D, McCance D R: The role of angiogenic and antiangiogenic factors in the second trimester in the prediction of preeclampsia in pregnant women with type 1 diabetes. Diabetes Care 2010; 36:3671-3677

Powers R W, Jeyabalan A, Clifton R G, Van Dorsten P, Hauth J C, Klebanoff M A, Lindheimer M D, Sibai B, Landon M, Miodovnik M: Soluble fms-Like tyrosine kinase 1 (sFlt1), endoglin and placental growth factor (PlGF) in preeclampsia among high risk pregnancies. PLoS One 2010; 5:e13263

Yu Y, Hanssen K F, Kalyanaraman V, Chirindel A, Jenkins A J, Nankervis A J, Torjesen P A, Scholz H, Henriksen T, Lorentzen B, Garg S K, Menard M K, Hammad S M, Scardo J A, Stanley J R, Wu M, Basu A, Aston C E, Lyons T J: Reduced soluble receptor for advanced glycation end-products (sRAGE) scavenger capacity precedes preeclampsia in Type 1 diabetes. Br J Obs Gyn 2012; 119:1512-1520

Yu Y, Jenkins A J, Nankervis A J, Hanssen K F, Scholz H, Henriksen T, Lorentzen B, Clausen T, Garg S K, Menard M K, Hammad S M, Scardo J C, Stanley J R, Dashti A, May K, Lu K, Aston C E, Wang J J, Zhang S X, Ma J X, Lyons T J: Anti-angiogenic factors and pre-eclampsia in type 1 diabetic women. Diabetologia 2009; 52:160-168.

CAVALCANTE MDE, S., TORRES-ROMERO, J. C., LOBO, M. D., MORENO, F. B., BEZERRA, L. P., LIMA, D. S., MATOS, J. C., MOREIRA RDE, A. & MONTEIRO-MOREIRA, A. C. 2016. A panel of glycoproteins as candidate biomarkers for early diagnosis and treatment evaluation of B-cell acute lymphoblastic leukemia. Biomark Res, 4, 1.

CODINA, R., VANASSE, A, KELEKAR, A, VEZYS, V. & JEMMERSON, R. 2010. Cytochrome c-induced lymphocyte death from the outside in: inhibition by serum leucine-rich alpha-2-glycoprotein-1. Apoptosis, 15, 139-52.

FURUKAWA, K, KAWAMOTO, K, EGUCHI, H., TANEMURA, M., TANIDA, T, TOMIMARU, Y, AKITA, H., HAMA, N., WADA, H., KOBAYASHI, S., NONAKA, Y, TAKAMATSU, S., SHINZAKI, S., KUMADA, T, SATOMURA, S., ITO, T, SERADA, S., NAKA, T, MORI, M., DOKI, Y, MIYOSHI, E. & NAGANO, H. 2015. Clinicopathological Significance of Leucine-Rich alpha2-Glycoprotein-1 in Sera of Patients With Pancreatic Cancer. Pancreas, 44, 93-8.

HA, Y. J., KANG, E. J., LEE, S. W, LEE, S. K, PARK, Y. B., SONG, J. S. & CHOI, S. T. 2014. Usefulness of serum leucine-rich alpha-2 glycoprotein as a disease activity biomarker in patients with rheumatoid arthritis. J Korean Med Sci, 29, 1199-204.

HAO, L., XIE, H., ZHANG, a, CHEN, D., WANG, S., ZHANG, H. & HE, S. 2016. LRG1 downregulation in allergic airway disorders and its expression in peripheral blood and tissue cells. J Transl Med, 14, 202.

HASHIDA, T, NAKADA, T. A, SATOH, M., TOMITA, K, KAWAGUCHI, R., NOMURA, F. & ODA, S. 2016.

Proteome analysis of hemofilter adsorbates to identify novel substances of sepsis: a pilot study. J Artif Organs.

HAUPT, H. & BAUDNER, S. 1977. [Isolation and characterization of an unknown, leucine-rich 3.1-S-alpha2-glycoprotein from human serum (author's transI)]. Hoppe Seylers Z Physiol Chem, 358, 639-46.

LYNCH, J., MEEHAN, M. H., CREAN, J., COPELAND, J., STALLINGS, R. L. & BRAY, I. M. 2013. Metastasis suppressor microRNA-335 targets the formin family of actin nucleators. PLoS One, 8, e78428.

MIYAJIMA, M., NAKAJIMA, M., MOTOI, Y, MORIYA, M., SUGANO, H., OGINO, I., NAKAMURA, E., TADA, N., KUNICHIKA, M. & ARAI, H. 2013. Leucine-rich alpha2-glycoprotein is a novel biomarker of neurodegenerative disease in human cerebrospinal fluid and causes neurodegeneration in mouse cerebral cortex. PLoS One, 8, e74453.

O'DONNELL, L. C., DRUHAN, L. J. & AVALOS, B. R. 2002. Molecular characterization and expression analysis of leucine-rich alpha2-glycoprotein, a novel marker of granulocytic differentiation. J Leukoc Biol, 72, 478-85.

SERADA, S., FUJIMOTO, M., TERABE, F., IIJIMA, H., SHINZAKI, S., MATSUZAKI, S., OHKAWARA, T., NEZU, R., NAKAJIMA, S., KOBAYASHI, T., PLEVY, S. E., TAKEHARA, T. & NAKA, T. 2012. Serum leucine-rich alpha-2 glycoprotein is a disease activity biomarker in ulcerative colitis. Inflamm Bowel Dis, 18, 2169-79.

TAKAHASHI, N, TAKAHASHI, Y. & PUTNAM, F. W. 1985. Periodicity of leucine and tandem repetition of a 24-amino acid segment in the primary structure of leucine-rich alpha 2-glycoprotein of human serum. Proc Nati Acad Sci USA, 82, 1906-10.

TAKEMOTO, N., SERADA, S., FUJIMOTO, M., HONDA, H., OHKAWARA, T, TAKAHASHI, T, NOMURA, S., INOHARA, H. & NAKA, T 2015. Leucine-rich alpha-2-glycoprotein promotes TGFbeta1-mediated growth suppression in the Lewis lung carcinoma cell lines. Oncotarget, 6, 11009-22.

WATSON, C. J., LEDWIDGE, M. T, PHELAN, D., COLLIER, P., BYRNE, J. C., DUNN, M. J., MCDONALD, K. M. & BAUGH, J. A. 2011. Proteomic analysis of coronary sinus serum reveals leucine-rich alpha2-glycoprotein as a novel biomarker of ventricular dysfunction and heart failure. Circ Heart Fail, 4, 188-97.

ZHANG, H., CAO, J., LI, L., LIU, Y, ZHAO, H., LI, N., LI, A., ZHANG, A, HUANG, H., CHEN, S., DONG, M., YU, L., ZHANG, J. & CHEN, L. 2015a. Identification of urine protein biomarkers with the potential for early detection of lung cancer. Sci Rep, 5, 11805.

ZHANG, Y, LUO, Q., WANG, N., HU, F., JIN, H., GE, T, WANG, C. & QIN, W. 2015b. LRG1 suppresses the migration and invasion of hepatocellular carcinoma cells. Med Oncol, 32, 146.

ZHONG, D., HE, G., ZHAO, S., LI, J., LANG, Y., YE, W., LI, Y., JIANG, C. & LI, X. 2015. LRG1 modulates invasion and migration of glioma cell lines through TGF-beta signaling pathway. Acta Histochem, 117, 551-8.

The invention claimed is:

1. An in vitro method of processing a biological sample from a pregnant subject at risk of developing a hypertensive disorder of pregnancy, the method comprising:
   obtaining a biological sample from the pregnant subject at risk of developing a hypertensive disorder of pregnancy, and
   detecting a level of leucine-rich alpha 2 glycoprotein 1 (LRG1) in said biological sample from said pregnant subject.

2. A method as claimed in claim 1 wherein the disorder is pre-eclampsia.

3. The method of claim 1, wherein the biological sample is whole blood, serum, plasma, urine, saliva or amniotic fluid.

4. The method as claimed in claim 1, wherein the biological sample is a sample obtained from the subject during a first trimester.

5. The method as claimed in claim 1, wherein the biological sample is a sample obtained from the subject during a second trimester.

6. The method as claimed in claim 1, wherein the biological sample is a sample obtained from the subject during a third trimester.

7. The method of claim 1 wherein the level of LRG1 is measured using an immunoreagent to detect the level of LRG1.

8. The method of claim 1, further comprising detecting said level of LRG1 in said biological sample with a test device comprising:

a housing a test strip contained within the housing, the test strip comprising one or more immunoreagents, wherein one of the one or more immunoreagents detects the level of LRG1.

9. The method of claim 7, wherein the immunoreagent that measures the level of LRG1 is an anti-LRG1 antibody.

10. The method of claim 9, the test device further comprising means for quantifying binding of the anti-LRG1 antibody to LRG1 in the biological sample.

* * * * *

SEQUENCE LISTING

```
Sequence total quantity: 2
SEQ ID NO: 1           moltype = AA  length = 16
FEATURE                Location/Qualifiers
REGION                 1..16
                       note = MISC_FEATURE - leucine-rich alpha 2 glycoprotein 1a
source                 1..16
                       mol_type = protein
                       organism = Homo sapiens
SEQUENCE: 1
GLKALGHLSG NRLRKL                                                              16

SEQ ID NO: 2           moltype = AA  length = 18
FEATURE                Location/Qualifiers
REGION                 1..18
                       note = MISC_FEATURE - leucine-rich alpha 2 glycoprotein 1b
source                 1..18
                       mol_type = protein
                       organism = Homo sapiens
SEQUENCE: 2
AGPEAVKGQT LLAVAKSQ                                                            18
```